United States Patent
Boland et al.

(10) Patent No.: US 9,956,163 B2
(45) Date of Patent: May 1, 2018

(54) FORMULATIONS FOR LIGHTENING SKIN AND TREATING HYPERPIGMENTATION

(71) Applicant: Colorescience, Inc., Carlsbad, CA (US)

(72) Inventors: Patricia McGill Boland, Houston, TX (US); Josie Juncal Schwarz, Carlsbad, CA (US); Deborah Eileen Gregg Bouche, Houston, TX (US)

(73) Assignee: COLORESCIENCE, INC., Carlsbad, CA (US)

( * ) Notice: Subject to any disclaimer, the term of this patent is extended or adjusted under 35 U.S.C. 154(b) by 413 days.

(21) Appl. No.: 14/735,778

(22) Filed: Jun. 10, 2015

(65) Prior Publication Data

US 2015/0359734 A1   Dec. 17, 2015

Related U.S. Application Data

(60) Provisional application No. 62/011,472, filed on Jun. 12, 2014.

(51) Int. Cl.
| | | |
|---|---|---|
| *A61K 8/99* | (2017.01) | |
| *A61K 8/27* | (2006.01) | |
| *A61K 8/29* | (2006.01) | |
| *A61K 8/67* | (2006.01) | |
| *A61Q 19/02* | (2006.01) | |
| *A61Q 17/04* | (2006.01) | |

(52) U.S. Cl.
CPC .................. *A61K 8/99* (2013.01); *A61K 8/27* (2013.01); *A61K 8/29* (2013.01); *A61K 8/678* (2013.01); *A61Q 19/02* (2013.01); *A61Q 17/04* (2013.01)

(58) Field of Classification Search
None
See application file for complete search history.

*Primary Examiner* — Amy L Clark
(74) *Attorney, Agent, or Firm* — Knobbe, Martens, Olson & Bear LLP

(57) ABSTRACT

Formulations to treat skin discoloration via a multi-modal approach are provided in which select ingredients work together to effectively brighten skin and treat hyperpigmentation. An example formulation includes a first anti-melanin agent, a second anti-melanin agent, an anti-inflammatory agent, a sun protection agent, and an anti-oxidant. In one aspect, the first anti-melanin agent comprises a *bidens pilosa* extract, the second anti-melanin agent comprises a *rheum rhaponticum* extract, the anti-inflammatory agent comprises a Vitamin E compound, the sun protection agent comprises zinc oxide and titanium dioxide, and the antioxidant comprises a *thermus thermophilus* ferment extract.

14 Claims, No Drawings

FORMULATIONS FOR LIGHTENING SKIN AND TREATING HYPERPIGMENTATION

This application claims the benefit of priority from U.S. Provisional Application No. 62/011,472, filed on Jun. 12, 2014, which is hereby incorporated by reference.

BACKGROUND

Primers, serums, lotions, and other cosmetic products are used on skin for various purposes. Cosmetic formulations can work like a moisturizer, or may absorb oil to create a matte appearance. Some can contain antioxidants, for example such as vitamin C and E or ingredients for moisturizing skin. For protection, some may even have a sun protection factor (SPF).

SUMMARY

Despite the large number of cosmetic formulations on the market, there remains a need for a cosmetic formulation that simultaneously reduces hyperpigmentation in a multi-modal manner and offers significant physical UVA and UVB sun protection, and optionally provides coverage (e.g., color) in a formulation that goes on smoothly and is not chalky or sticky. In many embodiments, the reduction of inflammation through the inclusion of an anti-inflammatory agent (e.g., vitamin E compounds) synergistically works with the other ingredients to counter hyperpigmentation via multiple pathways to enhance lightening and/or brightening effects.

Several embodiments of the present invention meet the need recited above. Several embodiments relate to unique skin care formulations for treating and protecting skin, including preventing further damage. Both healthy skin and damaged skin can benefit from several of the formulations described herein. Damaged skin can include skin with hyperpigmentation. Several embodiments are particularly useful for reducing specific regions of hyperpigmentation, thereby producing a brightening or lightening effect. An enhanced glow or radiance is achieved by several embodiments. Several formulations described herein are not limited to skin with hyperpigmentation. Indeed, many formulations are not only protective (for example by including a sun protection factor or SPF), but also nourish the skin, increase hydration and improve overall appearance, texture and firmness. Thus, several formulations of the invention are beneficial for skin that is aged, sun-damaged, wrinkled, lax, and/or blemished. Formulations according to several embodiments can be used anywhere on the body, and are especially beneficial for the face, neck, décolletage and hands, where hyperpigmentation and signs of aging may be particularly prominent.

In some embodiments, the invention comprises a topical formulation for treating and protecting skin in a subject, wherein the topical formulation is a liquid (such as a serum, lotion, liquid primer or cream), a gel, a spray, a powder, or a combination thereof.

In several embodiments, use of the formulations described herein reduces hyperpigmentation by about 10-100% (e.g., about 10%, 25%, 50%, 75%, 100% and ranges in between) after use. For example, significant lightening effects and improvements in pore size, fine lines, overall appearance, radiance, skin smoothness, and/or skin tone (evenness) are visible in several embodiments after 4 weeks, 8 weeks or 12 weeks. Certain improvements in skin may be visible or felt upon use or within days of use. Although specific regions of hyperpigmentation (e.g., age spots) are treated according to several embodiments, an overall lightening or brightening effect can also be achieved on skin that has no discrete regions of hyperpigmentation.

The topical formulation, in several embodiments, comprises or consists essentially of one or more anti-melanin agents (such as tyrosine inhibitors), one or more anti-inflammatory agents, and one or more sun protection agents. The anti-melanin agent(s) (such as tyrosine inhibitors) and anti-inflammatory agent(s) (such as vitamin E compounds) work synergistically together in many embodiments to counter undesired pigmentation.

In several embodiments, the formulation comprises (i) a first anti-melanin agent, (ii) a second anti-melanin agent, (iii) an anti-inflammatory agent, (iv) a sun protection agent, and (v) an optional anti-oxidant. In several embodiments, the formulation comprises about 0.05-5% of a first anti-melanin agent, about 0.005-5% of a second anti-melanin agent, about 0.05-5% of an anti-inflammatory agent, about 5-30% of a sun protection agent, and about 1-5% of an optional antioxidant, wherein the ranges are provided as % m/m, % m/v, or % v/v of the formulation. In some embodiments, the first anti-melanin agent comprises a *bidens pilosa* extract, the second anti-melanin agent comprises a *rheum rhaponticum* extract, the anti-inflammatory agent comprises a Vitamin E compound, the sun protection agent comprises zinc oxide and titanium dioxide offering a high sun protection factor (e.g., of SPF 30, 50 or more), and the antioxidant comprises a *thermus thermophilus* ferment extract. The formulation may additionally comprise some (e.g., 1-4) or all of the following oils in some embodiments: an *Elaeis Guineensis* oil, a *Gossypium Herbaceum* seed oil, a *Linum Usitatissimum* seed oil, a *Citrus Paradisi* seed extract, and a *Fusanus Spicatus* wood oil.

In several embodiments, the formulation comprises a *bidens pilosa* extract, an acetyl *rheum rhaponticum* root extract, a Vitamin E compound, a *thermus thermophilus* ferment extract, a zinc oxide, and a titanium dioxide, wherein the formulation provides a high sun protection factor of SPF 30, 50 or more. In some embodiments, the formulation comprises about 0.005-5% or about 0.05-5% *bidens pilosa*, about 0.005-5% or about 0.05-5% acetyl *rheum rhaponticum* root extract, about 0.05-5% Vitamin E compound, about 0.05-10%, about 5-15% zinc oxide, and about 10-15% titanium dioxide, wherein the ranges are provided as % m/m, % m/v, or % v/v of the formulation.

In several embodiments, the *rheum rhaponticum* extract comprises acetyl *rheum rhaponticum* root extract and the vitamin E compound comprises disodium lauriminodipropionate tocopheryl phosphates. The formulation may be a topical formulation in the form of e.g., a liquid, cream or gel, and in one embodiment is a paraben-free facial primer.

In several embodiments, a method of treating skin discoloration is provided, the method comprising identifying at least one region of a skin tissue having discoloration or an uneven tone (including but not limited to hyperpigmentation) and applying, or instructing application of, any one of the topical formulations described herein to the skin region, wherein the formulation lightens the hyperpigmentation and/or improves skin tone uniformity, as well as provides protection from ultraviolet rays, In some embodiments of the invention, the anti-melanin agents used herein directly and/or indirectly reduce the production of melanin, degrade melanin, reduce the melanin transfer from melanocytes to keratinocytes, and/or reduce the storage of melanin. In some embodiments, anti-melanin agents are tyrosinase inhibitors that inhibit the production and/or accumulation of melanin by inhibiting tyrosinase (which facilitates melanogenesis). Tyrosinase inhibitors used in the formulations described herein include but are not limited to one or more of the following: extracts from the rhubarb family (such as *rheum rhaponticum*, acetyl *rheum rhaponticum* root extract), ascorbic acid, bearberry, licorice, mulberry, kojic acid, green tea (picatechin gallate, epigallocatechin gallate and gallocatechin gallate) and acetylated hydroxystilbene. Tyrosinase inhibitors used in the formulations described herein also include but are not limited to polyphenols such as curcuminoids, flavonoids (e.g., anthocyanins, flavanols, flavanones, flavonols, flavones, isoflavones) and stilbenoids (e.g., resveratrol, pterolstilbene), free radical scavengers, and copper chelators. Anti-melanin agents used in the formulations described herein include tyrosinase inhibitors, as well as other agents that are not tyrosinase inhibitors but also have an ability to reduce the production of melanin, degrade melanin and/or reduce the storage of melanin (e.g., endothelin inhibitors). In some embodiments, the anti-melanin agent is a tyrosinase inhibitor comprising a *rheum rhaponticum* extract (e.g., acetyl *rheum rhaponticum* root extract) and a panthenol compound (e.g., panthenyl triacetate). In some embodiments, the anti-melanin agent is acetylated hydroxystilbene. The anti-melanin agents are provided, in several embodiments, in a range of about 0.001% to about 10% (e.g., 0.001%, 0.01%, 0.03%, 0.05%, 0.1%, 0.5%, 1%, 5%, 10%, and ranges in between) % m/m, % m/v, or % v/v in the formulation. In some embodiments, the panthenol compound (e.g., panthenyl triacetate) acts as an anti-irritant and anti-inflammatory. As discussed herein, reducing inflammation may reduce hyperpigmentation through an inflammatory-mediated pathway.

In several embodiments, at least two types of anti-melanin agents are included in a formulation. For example, one type reduces the production of melanin, while the other type(s) degrades (or enhance the degradation of) melanin, reduces the melanin transfer from melanocytes to keratinocytes, and/or reduces the storage of melanin. The use of at least two different anti-melanin agents provides synergistic effects in several embodiments. For example, in one embodiment, the formulation contains a *bidens pilosa* extract as an anti-melanin agent to beneficially affect melanin transport as well as a *rheum rhaponticum* extract (e.g., acetyl *rheum rhaponticum* root extract) as a tyrosinase inhibitor. These two extracts are combined with one or more anti-inflammatories and sun protection agents in many embodiments of the formulation to accomplish a multi-modal approach to effectively address the appearance of skin discoloration (e.g., hyperpigmentation, hypopigmentation, etc.). By affecting different points in the cascade of event that leads to discoloration, several embodiments of the formulation as described herein are particularly advantageous.

In some embodiments of the invention, the anti-inflammatory agents decrease redness and irritation (such as that caused by UV exposure) and fortify resistance to inflammation. The anti-inflammatory agents may have antioxidant properties by reacting with reactive oxygen species. The anti-inflammatory agents may also absorb the energy from UV light and are photo-protective, and reduce UV-induced free radical damage to skin. In several embodiments, the anti-inflammatory agents, by acting through a different pathway that involves inflammation's influence on pigmentation are particularly potent when combined with the anti-melanin agents. Post-inflammatory hyperpigmentation or hypermelanosis, which can occur after cutaneous inflammation or injury, is one example of hyperpigmentation that is related to inflammation, and according to several embodiments, is treated with the formulations described herein. Anti-inflammatory agents used in the formulations described herein include but are not limited to one or more of the following: vitamin E compounds (such as disodium lauriminodipropionate tocopheryl phosphate and other tocopherols), vitamin A compounds, vitamin B compounds, and vitamin D compounds. In several embodiments, the anti-inflammatory agent comprises a vitamin E compound (e.g., disodium lauriminodipropionate tocopheryl phosphate). The anti-inflammatory agents are provided, in several embodiments, in a range of about 0.1% to about 20% (e.g., 0.1%, 0.5%, 0.8%, 1%, 5%, 10%, 20%, and ranges in between) % m/m, % m/v, or % v/v in the formulation.

In some embodiments of the invention, the sun protection agents used have an SPF of 30, 50 or higher. In many embodiments, the sun protection agents are physical sunscreens (and not chemical sun screens) that block both UVA and UVB rays. The sun protection agents used in the formulations described herein include but are not limited to zinc oxide, titanium dioxide and other mineral oxides. The sun protection agents are provided, in several embodiments, in a range of about 2% to about 40% (e.g., 2%, 5%, 10%, 15%, 20%, 25%, 30%, 40%, and ranges in between) % m/m, % m/v, or % v/v in the formulation. In some embodiments, the formulations comprise 5-15% zinc oxide and 10-15% titanium dioxide. The terms sun protection agents, suncreens and sunblocks can be used interchangeably herein. Although physical suncreens are used in many embodiments, chemical suncreens may also be used.

In some embodiments, the formulation comprises or consists essentially of one or more anti-melanin agents (such as tyrosine inhibitors), one or more anti-inflammatory agents, and one or more sun protection agents and at least one of the following ingredients: a skin conditioning agent, a solvent, a silicone, an emollient, a preservative, a thickener, an antioxidant, and an excipient. Optional colorants and fragrances may additionally be included. Agents to adjust or balance pH may also be included.

According to several embodiments, a formulation for reducing hyperpigmentation is provided, said formulation comprising or consisting essentially of: one or more anti-melanin agents in an amount sufficient to reduce the synthesis of melanin; one or more anti-inflammatory agents in an amount sufficient to inhibit an inflammatory mediator involved in increasing melanin; and one or more agents that at least partially block ultraviolet rays. Optionally, one or more keratolytic agents in an amount sufficient to at last partially dissolve or soften the keratin is also included. In some embodiments, the ingredients act on hyperpigmentation through a different (but perhaps related) pathway and enhances the effectiveness of the formulation as a whole.

The topical formulation, in some embodiments, comprises or consists essentially of the following ingredients: about 0.05-5% (e.g., about 0.5-3%) vitamin E compound, 0.005-5% (e.g., about 0.03-3%) *rheum rhaponticum* extract (e.g., acetyl *rheum rhaponticum* root extract) and about 0.005-5% (e.g., about 0.03-3%) asteraceae extract (e.g., *bidens pilosa* extract). In addition, some or all of the following ingredients may be included: about 1-25% (e.g., about 5-30%) sunscreen and about 0.5-10% (e.g., about 1-5%) *thermus thermophillus* ferment. In addition, in some embodiments, at least one of the following ingredients is included: about 40-70% (e.g., about 50-65%) of a skin conditioning agent, about 5-20% (e.g., about 5-15%) of a solvent, such as water, about 0.5-15% (e.g., about 1-6%) of a water resistant agent/film forming agent. Emollients, humectants, preservatives, thickeners, binders, colorants, stabilizers, anti-foaming agents, and/or fragrances may additionally be included in the range of about 0.1-25%.

In several embodiments, the invention comprises or consists essentially of several or all of the following agents (or their respective derivatives, esters, acids, salts, and alcohols): one or more oxides or dioxides (e.g., titanium dioxide, zinc oxide, and/or iron oxide), one or more silicon/siloxane/silicone-based compounds (e.g., cyclopentasiloxane, dimethicone, dimethicone crosspolymer, trimethylsiloxysilicate, dimethicone/vinyl dimethicone crosspolymer, dimethiconol, cyclotetrasiloxane, and/or triethoxycaprylylsilane), one or more solvents (e.g., water), one or more triglycerides (e.g., caprylic/capric triglycerides), one or more bacterial, plant and/or fruit extracts (e.g., *thermus thermophillus* ferment, *rheum rhaponticum* extract such as acetyl *rheum rhaponticum* root extract, grapefruit seed extract, aster plant extract such as *bidens pilosa* extract, and/or *vanilla planifolia* fruit extract), one or more vitamin-based compounds such as panthenol, vitamin-E or vitamin-C based compounds (e.g., disodium lauriminodipropionate tocopheryl phosphates, tocopherol, tocotrienols, vitamin E, ascorbic acid, panthenol, and/or panthenyl triacetate), one or more oils (e.g., *fusanus spicata* wood oil, *elaeis guineensis* oil, *gossypium herbaceum* seed oil, *linum usitatissimum* seed oil), and one or more glycerin-based compounds (e.g., glycerin and/or glyceryl isostearate). Additionally, emulsifiers, surfactants and preservatives can be included (e.g., polyhydroxystearic acid, phenoxyethanol, potassium sorbate, dehydroacetic acid, and/or benzoic acid). Film formers may be used (such as acrylates, including acrylates/C12-22 alkyl methacrylate copolymer). Isocetyl stearoyl stearate may be used in some embodiments as a skin conditioning agent. Propylene or pentylene glycol (or other glycol) may be included as, for example, a humectant and/or solvent. Thickeners such as cellulose compounds (e.g. methycellulose) may be included. Ascorbic acid may function as a pH adjuster in some embodiments.

Although preservatives are provided in certain embodiments, the formulations described herein can be manufactured with reduced or no synthetic preservatives. In some embodiments, the formulations are free of one or more of the following: parabens, phthalates, sulfates, mineral oil, gluten, allergens, and irritants.

In several embodiments, the formulation comprises or consists essentially of Titanium Dioxide, Zinc Oxide, Cyclopentasiloxane, Isocetyl Stearoyl Stearate, Dimethicone Crosspolymer, *Thermus Thermophillus* Ferment, Water/Aqua/Eau, Dimethicone/Vinyl Dimethicone Crosspolymer, Disodium Lauriminodipropionate Tocopheryl Phosphates, Panthenyl Triacetate, Acetyl *Rheum Rhaponticum* Root Extract, *Bidens Pilosa* Extract, *Elaeis Guineensis* (Palm) Oil, *Gossypium Herbaceum* (Cotton) Seed Oil, *Linum Usitatissimum* (Linseed) Seed Oil, Tocopherol, Dimethiconol, *Citrus Paradisi* Seed Extract, Glycerin, Dimethicone, *Fusanus Spicatus* Wood Oil, *Vanilla Planifolia* Fruit Extract, Ascorbic Acid, Caprylic/Capric Triglyceride, Cyclotetrasiloxane, Propylene Glycol (or pentylene glycol or other glycol), Triethoxycaprylylsilane, Acrylates/C12-22 Alkyl Methacrylate Copolymer, Phenoxyethanol, Benzoic Acid, Dehydroacetic Acid, Potassium Sorbate, Farnesol, and Iron Oxides (CI 77491, CI 77492, CI 77499). Methylparaben may optionally be included, although in several embodiments, the formulation is free of methylparaben and/or other parabens.

The use of agents, ingredients and compounds may be used interchangeably herein. Reference to the term "based" includes the recited agent, ingredient or compounds. For example, a panthenol-based compound includes panthenol itself. The terms composition and formulation can be used interchangeably. Where percentages are provided for agents, ingredients and compounds, they can be % m/m, % m/v or % v/v with respect to the formulation as a whole, unless otherwise indicated, The agents, ingredients and compounds described herein may be modified natural substances (e.g., isolates, extracts, purified, processed, chemically modified, etc.) or synthetic substances. Methods of using unique combinations of natural substances are also provided.

In several embodiments, the invention comprises a method of treating skin using any one of the formulations described above or below. The use of any of the formulations described herein for treating skin (e.g., reducing hyperpigmentation) and/or improving skin appearance is provided in several embodiments. Several embodiments also include instructing the method or use of the formulation (e.g., via instructions for use).

DETAILED DESCRIPTION

As described above, several embodiments of the present invention relate to unique skin care formulations for treating and protecting skin. The formulations described herein can be beneficial for both healthy and damaged skin. In several embodiments, use of the formulations described herein provides one or more of the following advantages: (i) reduction in the appearance of redness, (ii) reduction in hyperpigmentation (e.g., reduction in age spots, discolored scar tissue, birthmarks, or other discoloration), (iii) skin looks and feels smoother; (iv) increased firmness, (v) increased hydration, (vi) improved skin tone and texture (e.g., increased evenness), (vii) clearer complexion, (viii) improved radiance, (ix) fine lines, pores, and wrinkles appear less visible, (x) improved overall appearance of skin, (xi) reinforcement of the skin's natural defenses, and (xii) improved epidermal structural integrity. Advantageously, in several embodiments, these improvements are obtained with formulations that are gentle and non-irritating, with no or little erythema, edema, dryness, peeling, itching, stinging, tingling, or burning sensation. Because undesired effects are nominal or nonexistent, the formulation fosters regular use by a subject, which enables longer term improvements in skin characteristics.

The formulations described herein can provide both short-term and long-term benefits according to several embodiments. Beneficial effects from use of the formulations described herein occur upon use, within hours of use, within 1-2 days, 3-4 days, about 7 days, about 14 days, or within about 3 weeks. In several embodiments, the skin characteristics continue to improve over about 2-4 weeks, about 4-6 weeks, about 6-10 weeks, or about 12-16 weeks of use.

Several embodiments of the invention comprise a formulation for protecting against UV damage and reinforcing the skin's natural defenses. In some embodiments, the formulation is in a liquid, gel or powder form. The formulations described herein can be applied prior to or after foundation or other make-up. In some embodiments, the formulation is colorless; however, in other embodiments, the formulation contains sufficient color to serve as foundation or cover-up. In some embodiments, the pH of the formulations is slightly basic, slightly acidic or neutral. In some embodiments, a pH of 3-5, 4-6, 5-7, 6-8, or ranges in between, are provided. Lower or higher pH values may also be used.

The formulations described herein have one or more of the following uses: primer, moisturizer, sunscreen, setting mist, and color (cover-up, coverage, or foundation). The unique aspects of many of the formulations described herein provide a multi-functional product that blends skin care and sun care, and offers a high SPF primer, color coverage, skin nourishment, anti-oxidants and a lightening effect (e.g., through a reduction of discoloration or pigmentation).

According to several embodiments, the formulations described herein can be applied by hand, by sponge, by spraying, by applicator, by brush, or through use of a composition-impregnated wipe or tissue. In some embodiments, the formulations are absorbent (e.g., readily absorbable) such that no separate means are needed to enhance absorption. However, in some embodiments, low frequency ultrasound, massage, application of an electrical field, mechanical manipulation or vibration may be used to facilitate absorption. In some embodiments, the formulation is useful post-surgery or dermatological treatment, where, for example, discoloration, may be an issue. Several topical formulations herein described can penetrate top layers of the skin. Further, some of the formulations described herein may be suitable for use for application under one or more skin layers (e.g., as an injectable).

The invention, according to several embodiments, comprises a topical formulation (such as an SPF liquid primer) for treating skin that includes *rheum rhaponticum* and *asteraceae*. In one embodiment, the *rheum rhaponticum* comprises acetyl *rheum rhaponticum* extract, extracted from the leaf, root, flower or other part of the plant. In one embodiment, the asteraceae comprises *bidens pilosa* extract from the leaf, root, flower or other part of the plant. *Rheum rhaponticum* and *bidens pilosa* are unrelated compounds that Applicant believes have unexpected synergistic effects in combination to reduce hyperpigmentation or otherwise treat skin. In addition to extracts of *rheum rhaponticum* and *bidens pilosa*, both vitamin E compounds and sunscreen are included in some embodiments. Vitamin E compounds, again unrelated to *rheum rhaponticum* and *bidens pilosa*, are believed to contribute synergistically with *rheum rhaponticum* and *bidens pilosa* for the treatment of skin, including the reduction of hyperpigmentation. For example, the synergistic combination of *rheum rhaponticum, bidens pilosa* and an anti-inflammatory agent (such as a Vitamin E compound) in some embodiments, decreases melanin synthesis, decreases accumulation of melanin in keratinocytes, and reduces inflammation and redness. Further, in some embodiments, the combination of an anti-melanin agent, such as a tyrosinase inhibitor, and and Vitamin E compounds or other anti-inflammatory agents synergistically decreases melanin synthesis, decreases accumulation of melanin in keratinocytes, and reduces inflammation and redness. In some embodiments, the *rheum rhaponticum* and the *bidens pilosa* are provided in the range of about 0.0005-10% and the vitamin E is provided in the range of about 0.05-10%. Sunscreen may be provided in the range of about 1-35%. Sunscreen provides an additional benefit by shielding the regions of hyperpigmentation from further pigmentation during the treatment process, thus facilitating the therapeutic benefits of the formulation. Further, sunscreen reduces the incidence of future hyperpigmentation and damage. In some embodiments, *thermus thermophillus* (e.g., *thermus thermophillus* ferment) is included with extracts of *rheum rhaponticum* and *bidens pilosa* and optionally Vitamin E compounds, sunscreen, and other ingredients. The *thermus thermophillus*, which is unrelated to *rheum rhaponticum, bidens pilosa* and vitamin E, is believed to provide further synergistic benefits to the combination of *rheum rhaponticum* and *bidens pilosa* (and optionally Vitamin E compounds). For example, *thermus thermophillus*, in some embodiments, acts as an antioxidant that is activated by heat and/or light thereby protecting against UV damage, which in turns preserves and reinforces the skin's natural defenses and improves epidermal structural integrity. *Thermus thermophillus* may also work as an anti-oxidant to supplement the vitamin E compound's ability to reduce inflammation, thereby reducing the effect of inflammation on increased pigmentation (e.g., through inflammatory mediators). To Applicant's knowledge, several combinations of ingredients disclosed herein represent unique formulations that are not naturally occurring (e.g., not found in nature in such combination). Moreover, in several embodiments, the individual ingredients are modified so as to be structurally and/or functionally different than the naturally-occurring species, thereby resulting in markedly unique effects.

In addition, in some embodiments, at least one of the following ingredients is included: a skin conditioning agent, a solvent, a silicone, an emollient, a preservative, a thickener, an antioxidant, an anti-inflammatory agent, and an excipient. Colorants and fragrances may additionally be included. In some embodiments, the formulation further includes one or more of the following: amino acids, peptides, phospholipids, additional vitamins, growth factors, and additional anti-aging compounds. Surfactants, gelling agents, and pH balancers may also be included.

In several embodiments, the formulation comprises a combination of various combination groups and individual ingredients. In some embodiments, the formulation comprises, consists essentially of or consists of several or all of the following groups of ingredients (or in certain cases of water and sandalwood, single ingredients):

(1) cyclopentasiloxane, dimethicone crosspolymer, dimethicone/vinyl dimethicone crosspolymer, dimethiconol, and cyclotetrasiloxane;

(2) zinc oxide and triethoxycaprylylsilane; or zinc oxide, caprylic/capric triglyceride, glyceryl isostearate, and polyhydroxy stearic acid;

(3) isocetyl stearoyl stearate or distilled water;

(4) acrylates/C12-22 alkyl methacrylate copolymer, water, and a glycol (such as propylene or pentylene glycol); or cyclopentasiloxane and trimethylsiloxysilicate;

(5) *thermus thermophillus* ferment, glycerin, phenoxyethanol, and potassium sorbate;

(6) titanium dioxide and dimethicone;

(7) disodium lauriminodipropionate tocopheryl phosphates, water, phenoxyethanol, dehydroacetic acid, and benzoic acid;

(8) panthenyl triacetate and acetyl *rheum rhaponticum* root extract;

(9) *bidens pilosa* extract, *elaeis guineensis* (palm) oil, *gossypium herbaceum* (cotton) seed oil, *linum usitatissimum* (linseed) seed oil, tocopherol;

(10) grapefruit seed extract, glycerin, ascorbic acid;

(11) iron oxides (CI 77491, CI 77492, CI 77499) and triethoxycaprylylsilane;

(12) *santalum spicatum* (sandalwood); and

(13) caprylic/capric triglyceride and *vanilla planifolia* fruit extract.

In one embodiment, group (1) above is provided in a range of about 30-80% (e.g., 30%, 50%, 60%, 70%, 80% and ranges in between) of the total formulation, with individual ranges (with respect to percentage amount vis-à-vis the select group of the following ingredients) as follows: cyclopentasiloxane (about 30%, 45%, 50%, 70%, 75% 80%, 82%, 85%, 90%, and ranges in between), dimethicone crosspolymer (about 6%, 8%, 10%, 12%, 14%, 20%, and ranges in between), dimethicone/vinyl dimethicone crosspolymer (about 1%, 2%, 3%, 6%, 10%, and ranges in between) dimethiconol (about 0.1%, 0.5%, 1%, 2%, 5%, and ranges in between) and cyclotetrasiloxane (about 0.1%, 0.5%, 1%, 2%, 5%, and ranges in between). By way of example, if cyclopentasiloxane is provided at 80% vis-à-vis the select group of compounds listed in group (1), and group (1) is provided as 60% of the total formulation, then cyclopentasiloxane will be present as 48% of the total formulation. In several embodiments, group (1) can further include or be substituted with elastomers, such as high molecular weight silicone elastomers, decamethylcyclopentasiloxane, phenyl silicons, alkylmethylsiloxanes, polydimethylsiloxanes, cross-linked silicone elastomer dispersions, hexamethyldisoilxane, cyclomethicone, and trimethylsilyamodimethicone, and combinations thereof. In several embodiments, group (1) can be a gel and be used in conditioning the skin, as well as for sebum absorption.

In one embodiment, group (2) and group (6) above are provided in a range of about 3-20% (e.g., 3%, 4%, 5%, 10%, 15%, 20%, and ranges in between) of the total formulation for group (2) and 0.5-25% (e.g., 0.5%, 1%, 2%, 3%, 5%, 10%, 15%, 20%, 25%, and ranges in between) of the total formulation for group (6). Individual ranges (with respect to percentage amount vis-à-vis the select group of the following ingredients) can be as follows for group (2): zinc oxide (about 20%, 30%, 40%, 50%, 60%, 70%, and ranges in between), caprylic/capric triglyceride (about 20%, 35%, 45%, 55%, 65%, 75%, and ranges in between), glyceryl isostearate (about 1%, 2%, 4%, 6%, 8%, and ranges in between) and polyhydroxy stearic acid (about 0.5%, 1%, 2%, 5%, and ranges in between). Alternatively, zinc oxide and triethoxycaprylylsilane are used instead. These two ingredients are used in the following amounts in several embodiments: zinc oxide (about 2%, 4%, 8%, 10%, 12%, 15%, 20%, and ranges in between) and triethoxycaprylylsilane (about 0.1%, 0.3%, 0.5%, 1%, 2%, 3%, and ranges in between). Individual ranges (with respect to percentage amount vis-à-vis the select group of the following ingredients) can be as follows for group (6): titanium dioxide (50, 60, 70, 80, 95, 96, 97, 98, 99%, and ranges in between) and dimethicone (about 1%, 2%, 4%, 6%, 8%, and ranges in between). According to several embodiments, zinc and titanium dioxide are used for UV absorption. Micronized and/or nanoscale zinc oxide together with titanium dioxide can be used and can provide strong protection against ultraviolet radiation and can be used in sunscreen, sunblock, tanning, and sun tanning lotions, creams, gels, and liquids according to several embodiments. Titanium dioxide can also be used herein as a pigment, sunscreen, sunblock and a thickener. Other ingredients that can be used in addition to or as a substitute for the ingredients in group (2) or (6) include but are not limited to, 4-methylbenzylidene camphor (Enzacamene, Parsol 5000, Eusolex 6300, MBC), Tinosorb M (bisoctrizole, methylene bis-benzotriazolyl tetramethylbutylphenol, MBBT), Tinosorb S (Bis-ethylhexyloxyphenol methoxyphenol triazine, bemotrizinol, BEMT, anisotriazine), Meroyl XL, (drometrizole trisiloxane), Benzophenone-9 (Uvinul DS 49, CAS 3121-60-6, Sodium Dihydroxy Dimethoxy Disulfobenzophenone), Uvinul T 150 (Octyl triazone, ethylhexyl triazone, EHT), Uvinul A Plus (Diethylamino Hydroxybenzoyl Hexyl Benzoate), Uvasorb HEB (Iscotrizinol, Diethylhexyl butamido triazone, DBT), Parsol SLX (Dimethico-diethylbenzalmalonate, Polysilicone-15), and Isopentenyl-4-methoxycinnamate (Isoamyl p-Methoxycinnamate, IMC, Neo Heliopan E1000, Amiloxate). In some embodiments, the formulations comprise 5-15% zinc oxide and 10-15% titananium dioxide.

In one embodiment, ingredient (3) above, water (e.g., distilled water), is provided in a range of about 1-20% (e.g., 1%, 2%, 3%, 4%, 5%, 10%, 12%, 15%, 20%, and ranges in between) of the total formulation. Alternatively, isocetyl stearoyl stearate is used instead or in addition to water in a range of about 5-20% (e.g., 5%, 10%, 12%, 15%, 20%, and ranges in between).

In one embodiment, group (4) above is provided in a range of about 0.5-10% of the total formulation (e.g., 0.5%, 1%, 2%, 3%, 4%, 5%, 6%, 10%, and ranges in between), with individual ranges (with respect to percentage amount vis-à-vis the select group of the following ingredients) as follows: cyclopentasiloxane (about 20%, 30%, 40%, 50%, 60%, 70%, and ranges in between) and trimethylsiloxysilicate (about 20%, 30%, 40%, 50%, 60%, 70%, and ranges in between). Alternatively, group (4) above is provided in a range of about 0.5-10% of the total formulation (e.g., 0.5%, 1%, 2%, 3%, 4%, 5%, 6%, 10%, and ranges in between), with individual ranges (with respect to percentage amount vis-à-vis the select group of the following ingredients) as follows: acrylates/C12-22 alkyl methacrylate copolymer (about 20%, 30%, 40%, 50%, 60%, 70%, and ranges in between), water (about 20%, 30%, 40%, 50%, 60%, 70%, and ranges in between), and a glycol, such as propylene or pentylene glycol (about 1%, 2%, 3%, 4%, 5%, 10%, and ranges in between).

In one embodiment, group (5) above is provided in a range of about 0.5-10% of the total formulation (e.g., 0.5%, 1%, 2%, 3%, 4%, 5%, 6%, 10%, and ranges in between), with individual ranges (with respect to percentage amount vis-à-vis the select group of the following ingredients) as follows: *thermus thermophillus*, such a *thermus thermophillus* ferment, (about 80%, 85%, 90%, 94%, 95%, 97%, 98%, 99%), glycerin (about 2%, 3%, 4%, 5%, 6%, 10%, and ranges in between), phenoxyethanol (about 0.1%, 0.5%, 1%, 2%, 5%, and ranges in between), and potassium sorbate (about 0.01%, 0.05%, 0.1%, 1%, 5%, and ranges in between). *Thermus thermophillus* can, according to several embodiments, function as an antioxidant activated by heat and light, to protect against UV damage, to preserve and reinforces the skin's natural defenses, and to improve epidermal structural integrity. *Thermus thermophillus* ferment is a product of the fermentation of *thermus thermophillus* and is one non-limiting example of the *thermus* genus than can be used herein. Other species include but are not limited to *T. antranikianii, T. aquaticus, T. brockianus, T. caldophilus, T. filiformis, T. igniterrae, T. kawarayuensis, T. nonproteolyticus, T. oshimai, T. rehai, T. scotoductus, T. yunnanensi,* and *T. manikaranii.* Fermented or non-fermented alternatives can be used.

In one embodiment, group (7) above is provided in a range of about 0.1-10% of the total formulation (e.g., 0.1%, 0.5%, 1%, 2%, 3%, 4%, 5%, 10%, and ranges in between), with individual ranges (with respect to percentage amount vis-à-vis the select group of the following ingredients) as follows: disodium lauriminodipropionate tocopheryl phosphates (about 20%, 40%, 60%, and ranges in between), water (about 20%, 40%, 55%, 59%, 65%, 70%, 80%, and ranges in between), phenoxyethanol (about 0.1%, 0.4%, 0.8%, 1.2%, 2%, 4%, and ranges in between), dehydroacetic acid (about 0.01%, 0.02%, 0.08%, 0.1%, 1%, 2%, 4%, and ranges in between), and benzoic acid (about 0.02%, 0.12%, 0.25%, 0.5%, 1%, 5%, and ranges in between). Disodium lauriminodipropionate tocopheryl phosphate serves, in several embodiments, as an antioxidant and an anti-inflammatory. In addition to, or in lieu of, disodium lauriminodipropionate tocopheryl phosphates, one or more of the following is provided: vitamin A, vitamin C, vitamin E, and beta-carotene.

In one embodiment, group (8) above is provided in a range of about 0.1-10% of the total formulation (e.g., 0.1%, 0.5%, 1%, 2%, 3%, 4%, 5%, 10%, and ranges in between), with individual ranges (with respect to percentage amount vis-à-vis the select group of the following ingredients) as follows: panthenyl triacetate (about 85%, 90%, 95%, 97%, 99%, and ranges in between) and acetyl *rheum rhaponticum* root extract (about 0.5%, 1%, 2%, 3%, 4%, 5%, 10%, 20%, and ranges in between). Panthenyl triacetate is an ingredient that, according to several embodiments, is used as an anti-irritant and an anti-inflammatory. It is a stable oil-soluble derivative of pantothenic acid and a member of the vitamin B complex. In several embodiments, this vitamin has soothing and anti-irritating properties on the skin, stimulates the cell proliferation and contributes to biological processes in skin metabolism. Pantothenic acid is a key molecule in Coenzyme A, an activator for many metabolic processes, and includes metabolic processes in the skin. Because of its lipophilic character, pantothenic acid is used herein in some embodiments to facilitate penetration of the formulation into the skin (e.g., via the sebaceous glands). In addition to, or in lieu of, panthenyl triacetate, other compounds related to panthenol may be used. Acetyl *Rheum rhaponticum* root extract is one non-limiting example of *rheum rhaponticum* that can be used herein to decrease melanin synthesis in melanocytes and its accumulation in keratinocytes.

In one embodiment, group (9) above is provided in a range of about 0.1-10% of the total formulation (e.g., 0.1%, 0.5%, 1%, 2%, 3%, 4%, 5%, 10%, and ranges in between), with individual ranges (with respect to percentage amount vis-à-vis the select group of the following ingredients) as follows: *bidens pilosa* extract (about 0.1%, 0.5%, 1%, 2% 3%, 5%, 7%, 10%, 15%, 30%, and ranges in between), *elaeis guineensis* (palm) oil (about 1%, 3%, 5%, 7%, 10%, 15%, 20%, 30%, and ranges in between), *gossypium herbaceum* (cotton) seed oil (about 1%, 3%, 5%, 7%, 10%, 15%, 20%, 30%, and ranges in between), *linum usitatissimum* (linseed) seed oil, (about 1%, 3%, 5%, 7%, 10%, 15%, 20%, 30%, and ranges in between), and tocopherol (about 1%, 3%, 5%, 7%, 10%, 15%, 20%, 30%, and ranges in between). Other species/sub-species of *elaeis, gossypium* and *linum* can also be used. Other botanical oils may be use in addition to or in lieu of the oils identified herein, including but not limited to coconut oil, walnut oil, avocado oil, castor oil, almond oil, grapeseed oil, olive oil, etc., and combinations thereof.

In one embodiment, group (10) above is provided in a range of about 0.01-5% of the total formulation (e.g., 0.01% 0.1%, 0.5%, 0.75%, 1%, 2%, 3%, 4%, 5%, and ranges in between), with individual ranges (with respect to percentage amount vis-à-vis the select group of the following ingredients) as follows: grapefruit seed extract such as *citrus paradisi* extract (about 2%, 4%, 6%, 8%, 10%), glycerin (about 75%, 80%, 85%, 87%, 90%, 95%, and ranges in between), ascorbic acid (about 1%, 3%, 5%, 7%, 10%, 15%, 20%, and ranges in between).

In one embodiment, (11) above is provided in a range of about 0.01-5% of the total formulation (e.g., 0.01% 0.1%, 0.5%, 0.75%, 1%, 2%, 3%, 4%, 5%, and ranges in between), with individual ranges (with respect to percentage amount vis-à-vis the select group of the following ingredients) as follows: iron oxides (about 90%, 95% 98%, 100%, and ranges in between) (CI 77491, CI 77492, CI 77499) and triethoxycaprylylsilane (about 1%, 2%, 3%, 4%, 5%, and ranges in between);

In one embodiment, ingredient (12) above, santalum *spicatum* (sandalwood), is provided in a range of about 0.001-3% (e.g., 0.001%, 0.01% 0.1%, 0.2%, 0.5%, 0.75%, 1%, 2%, 3% and ranges in between) of the total formulation. In several embodiments described herein, the formulation comprises sandalwood oil. Sandalwood oil is an essential oil that can be obtained, for example, from the steam distillation of chips and billets cut from the heartwood of the sandalwood tree. In several embodiments, sandalwood oil is used for skin conditioning. Santalum *spicatum* is one non-limiting example of sandalwood that may be used; other species of sandalwood can also be used. A combination of *fusanus spicatus* wood oil and farnesol are used in several embodiments.

In one embodiment, group (13) above is provided in a range of about 0.001-3% of the total formulation (e.g., 0.001%, 0.01% 0.1%, 0.5%, 0.75%, 1%, 2%, 3%, and ranges in between), with individual ranges (with respect to percentage amount vis-à-vis the select group of the following ingredients) as follows: caprylic/capric triglyceride (about 70%, 80%, 90%, 95%, and ranges in between) and *vanilla planifolia* fruit extract (about 5%, 8%, 10%, 12%, 15%, and ranges in between). *Vanilla* extract, such as *vanilla planifolia* fruit extract, can be used herein to give the formulations a pleasant fragrance and is one non-limiting example of a fragrance. Other fragrances can also be used, including lavender, lemon, orange, *gardenia*, jasmine, mint, and other flower and fruit extracts. Fragrance-free alternatives are also used herein.

In some embodiments, the groups of ingredients may be obtained as Dub SSIC, Dow 9546 Elastomer Blend, or Zano 10 Plus, Allianz OPT or paraben-free Alllianz OPT c5G, Venuceane, Tcote 031, Vital ET, Unilucent PA-13, Revinage, P-50 Liquid, Unipure Red, Yellow and Black, and *Vanilla* Extract K5035. In alternate embodiments, SolTerra Boost, Zinclear IM 50CCT, and/or Dow 749 Fluid may be optionally used.

In one embodiment, a thickener is provided in a range of about 0.1-10% of the total formulation (e.g., 0.1%, 0.5%, 1%, 2%, 3%, 4%, 5%, 10%, and ranges in between). The thickener can optionally include methycellulose in alternate embodiments.

In several embodiments, the formulation can have an SPF between 5 SPF and 100 SPF. In some embodiments, the topical composition can have an SPF of 15, 20, 25, 30, 35, 40, 45, 50, 60, 70, 80, 90, 100, and ranges in between. Greater SPF values may also be used in some embodiments. A physical sunscreen with an SPF of 50 is provided in several embodiments.

In several embodiments, the formulation comprises a stabilizer, suspending agent and/or thickener. Dimethicone crosspolymer is a silicon derivative that can be used herein as a stabilizing or a suspending agent or a thickener. Types of dimethicone crosspolymers that can be used as a stabilizing agent, suspending agent or a thickener include, but are not limited to, silicone CS-1600, which is a mixture between dimethicone crosspolymer and cyclopentasloxane, dimethicone crosspolymer 3, dimethycone crosspolymer PEG-8, cetyl dimethicone/dimethicone cross polymer, and dimethicone/vinyl dimethicone crosspolymer, and combinations thereof.

Glyceryl isostearate is a type of glyceryl monoester that can be used herein. Glyceryl isostearate can be used as a skin conditioning agent and an emollient. In several embodiments described herein, the topical composition can comprise an emollient. In several embodiments described herein, the topical composition can comprise a skin conditioning agent. In several embodiments described herein, the topical composition can comprise a glyceryl monoester. Glyceryl monoesters that can be used in skin care and treatment can also include, but are not limited to, glyceryl laurate, glyceryl laurate, glyceryl laurate/oleate, glyceryl adipate, glyceryl alginate, glyceryl arachidate, glyceryl behenate, glyceryl caprate, glyceryl caprylate, glyceryl caprylate/caprate, glyceryl citrate/lactate/linoleate/oleate, glyceryl cocoate, glyceryl collagenate, glyceryl erucate, glyceryl hydrogenated rosinate, glyceryl hydrogenated soyate, glyceryl hydroxystearate, glyceryl isopalmitate, glyceryl isostearate, glyceryl isostearate/myristate, glyceryl isostearates, glyceryl lanolate, glyceryl linoleate, glyceryl linolenate, glyceryl montanate, glyceryl myristate, glyceryl isotridecanoate/stearate/adipate, glyceryl oleate, glyceryl oleate/elaidate, glyceryl palmitate, glyceryl palmitate/stearate, glyceryl palmitoleate, gyceryl pentadecanoate, glyceryl polyacrylate, glyceryl rosinate, glyceryl sesquioleate, glyceryl/sorbitol oleate/hydroxystearate, glyceryl stearate/acetate, glyceryl stearate/maleate, glyceryl tallowate, glyceryl thiopropionate, and glyceryl undecylenate.

Polyhydroxystearic acid is a suspending agent and an emulsifier that is used to stabilize products. It can be used herein to suspend SPF protection components in lotions, liquids and gels.

Decamethylcyclopentasiloxane is a cyclopentasiloxane, a silicone fluid that can be used herein. It can work as an emollient for the skin. Trimethylsiloxysilicate can be used for an antifoaming agent, an emollient, and/or for conditioning the skin. In some embodiments, trimethylsiloxysilicate is a cross-linked silicone resin with film-forming attributes. It can hold pigments in place while providing water-resistance in some embodiments. In some formulations herein, it provides a long-lasting effect. In several embodiments, trimethylsiloxysilicate may reduce the number of times the formulation needs to be applied. Trimethylsiloxysilicate is a siloxane polymer. Other examples of siloxane polymers that can be used herein include silica silylate, silica dimethyl silylate, and trifluoropropyldimethyl/trimethylsiloxysicate. In some embodiments, they are insoluble in water and used for film forming, wear and water resistance. In several embodiments described herein, the formulation comprises a siloxane polymer.

Glycerin is also known as glycerol, or glycerine. It is a viscous liquid used in pharmaceutical formulations and cosmetic formulations. Glycerin comprises a glycerol backbone, and is central to all lipids and commonly known as a triglyceride. Several types of triglycerides can be used herein. These can be for example, caprylic/capric triglycerides, triglycerides with C10-C18 fatty acid chains, and triglycerides with C18-C36 fatty acid chains. Fatty acids can include for example, naturally occurring fatty acids which can vary in chain length from 6 to 24 carbon atoms, and can include both saturated and unsaturated fatty acids containing one or more double bonds, and other fatty acids that are known to those skilled in the art. Triglycerides are used herein in some embodiments as an emollient for the skin.

Preservatives such as grapefruit seed extract, benzoic acid, dehydroacetic acid, phenoxyethanol and potassium sorbate are used in several embodiments of the formulations. Preservatives can be naturally occurring, modified, or synthetically produced. In addition to, or in lieu of the preservatives recited above, the following may be used: fermented radish root, rosemary oleoresin extract, salicylic acid, sorbic acid (hexa-2,4-dienoic acid), biphenyl-2-ol (o-phenylphenol), zinc pyrithione, inorganic sulphites, hydrogensulphites, chlorobutanol, 4-hydroxybenzoic acid, 3-acetyl-6-methylpyran-2,4 (3h)-dione (dehydroacetic acid) and its salts, formic acid and its sodium salt, 3,3'-dibromo-4,4'-hexamethylenedioxydibenzamidine (dibromohexamidine) and its salts (including isethionate), thiomersal (inn), phenylmercuric salts (including borate), undec-10-enoic acid and salts, hexetidine, 5-bromo-5-nitro-1,3 dioxane, bronopol, 2,4-dichlorobenzyl alcohol, triclocarban, 4-chloro-m-cresol, triclosan, 4-chloro-3,5-xylenol, 3,3'-bis(1-hydroxymethyl-2,5-dioxoimidazolidin-4-yl)-1,1'-methylenediurea, poly(1-hexamethylenebiguanide hydrochloride), 2-phenoxyethanol, hexamethylenetetramine (methenamine), methenamine 3-chloroallylochloride, 1-(4-chlorophenoxy)-1-(imidazol-1-yl) 3,3-dimethylbutan-2-one, 1,3-bis(hydroxymethyl)-5,5-dimethylimidazolidine-2,4-dione, benzyl alcohol, 1-hydroxy-4-methyl-6(2,4,4-trimethylpentyl)-2-pyridon, 6,6-dibromo-4,4-dichloro-2,2'-methylenediphenol: bromochlorophen, 4-isopropyl-m-cresol, mixture of 5-chloro-2-methylisothiazol-3(2h)-one and 2-methylisothiazol-3(2h)-one with magnesium chloride and magnesium nitrate, 2 benzyl-4-chlorophenol, 2-chloroacetamide, chlorhexidine (inn) and its digluconate, diacetate and dihydrochloride, 1-phenoxypropan-2-ol, alkyl (c12-c22) trimethyl ammonium, bromide and chloride, 4,4-dimethyl-1,3-oxazolidine, n-(hydroxymethyl)-n-(dihydroxymethyl-1,3-dioxo-2, 5-imidazolinidyl-4)-n'-(hydroxymethyl) urea, 1,6-di(4-amidinophenoxy)-n-hexane (hexamidine) and its salts (including isethionate and p-hydroxy-benzoate, glutaraldehyde (pentane-1,5-dial), 5-ethyl-3,7-dioxa-1-azabicyclo [3.3.0]octane, 3-(p-chlorophenoxy)-propane-1,2-diol (chlorphenesin), sodium hydroxymethylamino acetate (sodium hydroxymethylglycinate), silver chloride deposited on titanium dioxide, benzethonium chloride, benzalkonium chloride, bromide and saccharinate, benzylhemiformal, iodopropynyl butyl-carbamate, 3-iodo-2-propynylbutylcarbamate, methylisothiazolinone, and combinations thereof. Anti-fungal preservatives and/or anti-bacterial preservatives may be used.

In several embodiments described herein, the topical formulation comprises *bidens pilosa* extract to beneficially affect melanin transport. In other embodiments, this extract can help improve skin radiance and texture by, for example, encouraging cell turnover and may have retinoid-like activity. *Bidens pilosa* extract can be combined with various oils and tocopherol in several embodiments. For example, *Elaeis guineensis* (palm) oil comes from a palm species. This vegetable excipient can be used as a skin conditioning agent and as an emollient. *Gossypium herbaceum* (cotton) seed oil is a vegetable excipient. Cottonseed oil and ingredients made from cottonseed oil can be used herein as excipients with emollient properties. *Linum usitatissimumn* (linseed) seed oil also known as flaxseed oil can be obtained from the dried, ripened seeds of the flax plant and can function as an excipient and/or a skin-conditioning agent herein. Tocopherol is a vitamin E compound, with benefits described herein.

*Bidens pilosa* extract combined with acetyl *rheum rhaponticum* root extract work synergistically in several embodiments to enhance the anti-melanin effects. In some embodiments, the ratio of *bidens pilosa* and a *rheum rhaponticum* extract is 1:1, 1:2, 1:3, 1:4, 1:5, 1:10, 1:25, and ranges in between. In some embodiments, the ratio of the *rheum rhaponticum* extract and *bidens pilosa* is 1:1, 1:2, 1:3, 1:4, 1:5, 1:10, 1:25, and ranges in between. The two agents when combined work synergistically as anti-melanin agents, and further when combined with vitamin E compounds, provide enhanced synergy with the anti-inflammatory effects. Additionally, when combined with a high SPF (such as SPF 30, 50 or more), the formulations' effects on lightening skin are further pronounced. In some embodiments, the ratio of vitamin E compounds (or other anti-inflammatory agents) to the anti-melanin agent(s) is 1:1, 2:1, 3:1, 4:1, 5:1, 10:1, 25:1, and ranges in between.

As described herein, anti-inflammatory agents other than vitamin E compounds can be used in addition to, or in lieu of, vitamin E compounds. Anti-inflammatory agents are used, in some embodiments, to inhibit the inflammatory pathway that can affect melanin. For example, during the inflammatory process in the epidermal layer, inflammatory mediators (such as cytokines, chemokines, prostanoids such as prostaglandins, reactive oxygen species, etc.) may be released. The inflammatory mediators, in turn, may stimulate melanocytes to affect the production, sequestering, and/or processing of melanin in a manner that contributes to hyperpigmentation. An anti-inflammatory agent, as used herein in several embodiments, interrupts (e.g., or otherwise inhibits) this pathway, which in turn helps to reduce hyperpigmentation. In some embodiments, the balancing of inflammation and inflammatory pathways is accomplished.

In several embodiments, the invention comprises or consists essentially of cyclopentasiloxane, isocetyl stearoyl stearate, dimethicone crosspolymer, *thermus thermophillus* ferment, water/aqua/eau, dimethicone/vinyl dimethicone crosspolymer, disodium lauriminodipropionate tocopheryl phosphates, panthenyl triacetate, acetyl *rheum rhaponticum* root extract, dimethiconol, *citrus paradisi* seed extract, glycerin, dimethicone, *fusanus spicatus* wood oil, *vanilla planifolia* fruit extract, caprylic/capric triglyceride, *elaeis guineensis* (palm) oil, *bidens pilosa* extract, *gossypium herbaceum* (cotton) seed oil, *linum usitatissimum* (linseed) seed oil, tocopherol, cyclotetrasiloxane, a glycol (such as propylene or pentylene glycol), acrylates/C12-22 alkyl methacrylate copolymer, ascorbic acid, phenoxyethanol, benzoic acid, dehydroacetic acid, potassium sorbate, triethoxycaprylylsilane, farnesol, and iron oxides (e.g., CI 77491, CI 77492, CI 77499).

In several embodiments, the invention comprises or consists essentially of cyclopentasiloxane, isocetyl stearoyl stearate, dimethicone crosspolymer, *thermus thermophillus* ferment, water/aqua/eau, dimethicone/vinyl dimethicone crosspolymer, disodium lauriminodipropionate tocopheryl phosphates, panthenyl triacetate, acetyl *rheum rhaponticum* root extract, dimethiconol, *citrus paradisi* seed extract, glycerin, dimethicone, *fusanus spicatus* wood oil, *vanilla planifolia* fruit extract, caprylic/capric triglyceride, *elaeis guineensis* (palm) oil, *bidens pilosa* extract, *gossypium herbaceum* (cotton) seed oil, *linum usitatissimum* (linseed) seed oil, tocopherol, cyclotetrasiloxane, a glycol (such as propylene or pentylene glycol), acrylates/C12-22 alkyl methacrylate copolymer, ascorbic acid, phenoxyethanol, benzoic acid, dehydroacetic acid, potassium sorbate, triethoxycaprylylsilane, farnesol, titanium dioxide (CI 77891), zinc oxide (CI 77947), iron oxides (e.g., CI 77491, CI 77492, CI 77499).

In several embodiments, the invention comprises or consists essentially of titanium dioxide, zinc oxide, cyclopentasiloxane, water (aqua), dimethicone crosspolymer, caprylic/capric triglycerides, trimethylsiloxysilicate, *thermus thermophillus* ferment, dimethicone/vinyl dimethicone crosspolymer, methycellulose, panthenyl triacetate, acetyl *rheum rhaponticum* root extract, disodium lauriminodipropionate tocopheryl phosphates, grapefruit seed extract, *bidens pilosa* extract, *fusanus spicata* wood oil, *elaeis guineensis* (palm) oil, tocopherol, *gossypium herbaceum* (cotton) seed oil, *linum usitatissimum* (linseed) seed oil, glycerin, glyceryl isostearate, dimethiconol, cyclotetrasiloxane, triethoxycaprylylsilane, ascorbic acid, *vanilla planifolia* fruit extract, dimethicone, polyhydroxy stearic acid, phenoxyethanol, potassium sorbate, dehydroacetic acid, benzoic acid, and iron oxides (e.g., CI 77491, CI 77492, CI 77499).

The topical formulations described herein may be used as a primer. In addition, according to several embodiments, the formulations may be foundation, blush, lip color, eye color, lotions, creams, serums, gels, cleansing formulations, eye creams, sunscreens, bronzers, powders, nail care, hair care, and other cosmetics and skin care products.

According to several embodiments, the ingredients may be delivered in a single formulation or separately. For example, the anti-melanin agent and the anti-inflammatory agent and sunscreen can be in a single formulation. Alternatively, the ingredients or groups of ingredient may be provided in separate compositions. For example, the anti-melanin agent(s) and the anti-inflammatory agent(s) may be in one formulation and the sunscreen in another. The topical formulations are, according to several embodiments, applied once a day, twice a day, or every other day. Greater frequencies may also be used. Lesser frequencies may also be used, for example in maintenance phase after the desired effects have been achieved. Multi-chamber dispensers can be used in some embodiments. In several embodiments, a kit comprising a formulation and one or more skin care or cosmetic products is provided. In one embodiment, the kit comprises the anti-melanin and anti-inflammatory agents in one unit and the sunscreen separately. In one embodiment, the kit comprises the anti-melanin and anti-inflammatory agents in one formulation and, optionally, a separate keratolytic. Applicators (brushes, sticks, sponges, etc.) may be provided to apply the formulations described herein, and may also be included in a kit. The kit can comprise one or more of the formulations described herein in varying strengths (e.g., of the active ingredients). The kit can comprise one or more of the formulations described herein as well as an addition sunscreen and/or exfoliant.

In several embodiments, hyperpigmentation is reduced by 10-100% after use. For example, significant lightening effects and improvements in pore size, fine lines, overall appearance, radiance, skin smoothness, and/or skin tone (evenness) are visible in several embodiments after 4 weeks, 8 weeks and 12 weeks. Certain improvements in skin may be visible or felt upon use or within days of use. Although specific regions of hyperpigmentation are treated according to several embodiments, an overall lightening or brightening effect can also be achieved on skin that has no identifiable regions of hyperpigmentation.

Several embodiments of the formulations are particularly advantageous because they provide coverage (e.g., color, camouflage) in a formulation that goes on smoothly and is not chalky or sticky. This is helpful to cover areas of hyperpigmentation while the formulation is simultaneously working to reduce said hyperpigmentation. This is also helpful to minimize the number of products a user applies to his/her face (or body) because it reduces the need for a separate foundation.

Several embodiments of the formulations are water resistant. In one embodiment, the formulation is water resistant, e.g., with respect to SPF, for up to 30, 40, 60 and 120 minutes. Long-wear formulations are provided in several embodiments.

The formulations, according to several embodiments, are especially effective because they offer a multi-modal approach to reduction of hyperpigmentation. The combination of the anti-melanin agent with the anti-inflammatory and sunscreen provides a multi-modal approach that addresses discoloration via multiple pathways and results in the creation of a unique and effective formulation. In several embodiments, the anti-inflammatory agents, by acting through a pathway that involves inflammation's role in hyperpigmentation, are particularly effective when combined with the anti-melanin agents.

In some embodiments, one or more keratolytic agents may be optionally included. For example, one embodiment comprises or consists essentially of one or more keratolytic agents, one or more anti-melanin agents (such as tyrosine inhibitors), one or more anti-inflammatory agents, and one or more sun protection agents. The keratolytic agent(s), anti-melanin agent(s) (such as tyrosine inhibitors), and anti-inflammatory agent(s) (such as vitamin E compounds) work synergistically together in many embodiments to counter undesired pigmentation. The keratolytic agents used herein can, in one embodiment, break down the keratinized outer layer of the epidermis. Keratolytic agents may help remove or soften older, damaged surface tissue (e.g., keratin) and promote the generation of new skin cells. In several embodiments, keratolytic agents are retinoid-like compounds (such as from a vegetable or botanical source), improve skin radiance and texture, produce a lightening effect, reduce melanin, and or restore firmness. Keratolytic agents used in the formulations described herein include but are not limited to one or more of the following: extracts from the aster family of plants (such as asteraceae, *bidens pilosa*), salicylic acid, alpha hydroxy acid, beta hydroxy acid, sulfur, azelaic acid, glycolic acid, urea, lactic acid, resorcinol, allantoin, and fruit acids. In some embodiments, the keratolytic agent includes *bidens pilosa* extract, and one or all of palm oil, cottonseed oil, linseed oil and tocopherol. In some embodiments, exfoliants are used in addition to or in lieu of keratolytic agents. Exfoliants can be chemical or mechanical. The keratolytic agents are provided, in several embodiments, in a range of about 0.005% to about 10% (e.g., 0.005%, 0.05%, 0.1%, 0.5%, 1%, 5%, 10%, and ranges in between) % m/m, % m/v, or % v/v in the formulation. In some embodiments, the ratio of the keratolytic and the anti-melanin agent is 1:1, 1:2, 1:3, 1:4, 1:5, 1:10, 1:25, and ranges in between. In some embodiments, the ratio of the anti-melanin agent and the keratolytic is 1:1, 1:2, 1:3, 1:4, 1:5, 1:10, 1:25, and ranges in between. Although *bidens pilosa* may have keratolytic properties in some aspects, several embodiments include *bidens pilosa* for its anti-melanin properties rather than its keratolytic properties.

In one embodiment, the formulation comprises or consists essentially of some or all of the following agents in the percentage ranges (vis-à-vis the formulation as a whole) provided:

| Agent | Approximate % Amount in Formulation |
|---|---|
| Siloxane (e.g., Cyclopentasiloxane) | 30-60% |
| Titanium Dioxide | 5-20% |
| Isocetyl Stearoyl Stearate | 5-20% |
| Zinc Oxide | 2-15% |
| Dimethicone Crosspolymer | 2-10% |
| Thermus Thermophillus Ferment | 1-5% |
| Water/Aqua/Eau | 1-5% |

-continued

| Agent | Approximate % Amount in Formulation |
|---|---|
| Dimethicone/Vinyl Dimethicone Crosspolymer | 0.5-5% |
| Iron Oxides | 0.5-5% |
| Panthenyl Triacetate | 0.1-5% |
| Acrylates/C12-22 Alkyl Methacrylate Copolymer | 0.1-5% |
| Vitamin E Compound (e.g., Disodium Lauriminodipropionate Tocopheryl Phosphates) | 0.1-5% |
| Dimethiconol | 0.1-5% |
| Cyclotetrasiloxane | 0.1-5% |
| Glycerin | 0.05-5% |
| Dimethicone | 0.05-5% |
| Elaeis Guineensis (Palm) Oil | 0.05-5% |
| Gossypium Herbaceum (Cotton) Seed Oil | 0.05-5% |
| Citrus Paradisi (Grapefruit) Seed Extract | 0.05-5% |
| Triethoxycaprylylsilane | 0.05-5% |
| Bidens Pilosa Extract | 0.05-5% |
| Linum Usitatissimum (Linseed) Seed Oil | 0.05-5% |
| Fusanus Spicatus Wood Oil, Farnesol | 0.05-5% |
| Ascorbic Acid | 0.05-5% |
| Glycol (e.g., Pentylene or Propylene Glycol) | 0.05-5% |
| Caprylic/Capric Triglyceride | 0.05-5% |
| Phenoxyethanol | 0.01-5% |
| Rheum Rhaponticum (e.g., Acetyl Rheum Rhaponticum Root Extract) | 0.005-5% |
| Vanilla Extract (e.g., Vanilla Planifolia Fruit Extract) | 0.001-5% |
| Potassium Sorbate | 0.0005-5% |
| Benzoic Acid | 0.0005-5% |
| Dehydroacetic Acid | 0.0005-5% |
| Tocopherol | 0.0001-5% |

With respect to the use of substantially any plural and/or singular terms herein, those having skill in the art can translate from the plural to the singular and/or from the singular to the plural as is appropriate to the context and/or application.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. For example, "an" agent can include one, two or several ingredients (and not necessarily a single ingredient). In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth. The phrases "and ranges in between" can include ranges that fall in between the numerical values listed. For example, "1, 2, 3, 10, and ranges in between" can include 1-10, 1-3, 2-10, etc.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

For the methods disclosed herein, the functions performed in the processes and methods may be implemented in differing order. The disclosure of methods or uses may also include instructing the method or use (for example, in instructions for use).

The use of agents, ingredients and compounds may be used interchangeably herein. Reference to "based" agents, ingredients and compounds include the recited agent, ingredient or compounds. For example, a panthenol-based compound includes panthenol itself.

What is claimed is:

1. A high SPF (sun protection factor) formulation for treating skin discoloration, comprising effective amounts of:
a *bidens pilosa* extract;
an acetyl *rheum rhaponticum* root extract;
a Vitamin E compound;
a *thermus thermophilus* ferment extract;
zinc oxide; and
titanium dioxide,
wherein said formulation provides a sun protection factor of SPF 50 or more; and
wherein the formulation is a topical formulation in the form of a liquid, cream or gel.

2. The formulation of claim 1, wherein the vitamin E compound is disodium lauriminodipropionate tocopheryl phosphate.

3. The formulation of claim 1, wherein said formulation is a paraben-free facial primer.

4. A high SPF (sun protection factor) formulation for treating skin discoloration, comprising effective amounts of:
(i) a first anti-melanin agent,
wherein said first anti-melanin agent comprises a *bidens pilosa* extract;
(ii) a second anti-melanin agent,
wherein said second anti-melanin agent comprises a *rheum rhaponticum* extract;
(iii) an anti-inflammatory agent,
wherein said anti-inflammatory agent comprises a Vitamin E compound;
(iv) a sun protection agent,
wherein said sun protection agent comprises zinc oxide and titanium dioxide,
wherein said sun protection agent offers a sun protection factor of SPF 50 or more; and
wherein the formulation is a topical formulation suitable for topical delivery.

5. The formulation of claim 4, further comprising an antioxidant.

6. The formulation of claim 5, wherein the antioxidant comprises a *thermus thermophilus* ferment extract.

7. The formulation of claim 4, wherein the *rheum rhaponticum* extract comprises acetyl *rheum rhaponticum* root extract.

8. The formulation of claim 4, wherein the vitamin E compound is disodium lauriminodipropionate tocopheryl phosphates.

9. The formulation of claim 4, wherein said formulation is a paraben-free facial primer.

10. The formulation of claim 1, wherein said formulation further comprises *Elaeis Guineensis* oil, *Gossypium Herbaceum* seed oil, *Linum Usitatissimum* seed oil, *Citrus Paradisi* seed extract, and *Fusanus Spicatus* wood oil.

11. The formulation of claim 1, wherein the amount of the *bidens pilosa* extract in the formulation is 0.05-5%, and wherein the amount of the acetyl *rheum rhaponticum* root extract in the formulation is 0.005-5%.

12. The formulation of claim 1, wherein the amount of the *bidens pilosa* extract in the formulation is 0.005-5%, the amount of the acetyl *rheum rhaponticum* root extract in the formulation is 0.005-5%, the amount of the Vitamin E compound in the formulation is 0.05-5%; the amount of the *thermus thermophilus* ferment extract in the formulation is 0.05-10%; the amount of the zinc oxide in the formulation is 5-15%; and the amount of the titanium dioxide in the formulation is 10-15%.

13. The formulation of claim 4, wherein the amount of the first anti-melanin agent in the formulation is 0.05-5%, the amount of the second anti-melanin agent in the formulation is 0.005-5%, the amount of the anti-inflammatory agent in the formulation is 0.05-5%, the amount of the zinc oxide in the formulation is 5-15%, and the amount of the titanium dioxide in the formulation is 10-15%.

14. The formulation of claim 4, wherein said formulation further comprises *Elaeis Guineensis* oil, *Gossypium Herba-*

*ceum* seed oil, *Linum Usitatissimum* seed oil, *Citrus Paradisi* seed extract, and *Fusanus Spicatus* wood oil.

\* \* \* \* \*